(12) United States Patent
Salm et al.

(10) Patent No.: US 10,013,752 B2
(45) Date of Patent: *Jul. 3, 2018

(54) VIRTUAL BLADE INSPECTION

(71) Applicant: General Electric Company, Schenectady, NY (US)

(72) Inventors: Jacob Andrew Salm, Mauldin, SC (US); Onat Bas, Istanbul (TR); Birol Turan, Istanbul (TR)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/355,202

(22) Filed: Nov. 18, 2016

(65) Prior Publication Data

US 2018/0144457 A1    May 24, 2018

(51) Int. Cl.
   *G06K 9/00*   (2006.01)
   *G06T 7/00*   (2017.01)
   (Continued)

(52) U.S. Cl.
   CPC .......... *G06T 7/0004* (2013.01); *F01D 21/003* (2013.01); *G01B 11/002* (2013.01);
   (Continued)

(58) Field of Classification Search
   None
   See application file for complete search history.

(56) References Cited

U.S. PATENT DOCUMENTS 2,977,533 A    3/1961    Savage
3,473,231 A    10/1969   Herman
(Continued)

FOREIGN PATENT DOCUMENTS

CN    101566455 A    10/2009
CN    101791765 A    8/2010
(Continued)

OTHER PUBLICATIONS

Makem at al, A virtual inspection framework for precision manufacturing of aerofoil components, Computer-Aided Design, vol. 44, Issue 9, Sep. 2012, pp. 858-874.*

(Continued)

*Primary Examiner* — Andrae S Allison
(74) *Attorney, Agent, or Firm* — Ernest G. Cusick; Hoffman Warnick LLC

(57) ABSTRACT

A system and method for virtually inspecting a blade stage is disclosed. The system may include a digitizing device for obtaining a three-dimensional model of a shroud of each blade of the blade stage. A computer system may include at least one module configured to perform the following processes: extract a geometric location data of a plurality of reference points of each shroud from a three-dimensional model of a shroud of each blade of the blade stage created by digitizing using a digitizing device; generate a 3D virtual rendering of the shrouds of the blade stage based on the geometric location data and the known dimensions of the blade stage, the three-dimensional virtual rendering including a rendering of the plurality of reference points of each shroud; and inspect the blade stage using the three-dimensional virtual rendering.

20 Claims, 10 Drawing Sheets

(51) Int. Cl.
*G06T 7/60* (2017.01)
*G01B 11/16* (2006.01)
*G01B 11/00* (2006.01)
*G01N 21/88* (2006.01)
*F01D 21/00* (2006.01)

(52) U.S. Cl.
CPC ......... *G01B 11/16* (2013.01); *G01N 21/8851* (2013.01); *G06T 7/004* (2013.01); *G06T 7/60* (2013.01); *G01N 2201/12* (2013.01); *G06T 2200/04* (2013.01); *G06T 2200/08* (2013.01); *G06T 2207/30164* (2013.01)

(56) References Cited

U.S. PATENT DOCUMENTS

| | | | |
|---|---|---|---|
| 4,333,239 A | 6/1982 | Arrigoni | |
| 5,133,643 A | 7/1992 | Ortolano | |
| 5,162,659 A * | 11/1992 | Diamond | G01B 11/02 250/559.13 |
| 6,346,941 B1 | 2/2002 | Arita et al. | |
| 6,701,616 B2 * | 3/2004 | Smith | B23P 6/007 29/402.09 |
| 6,792,655 B2 * | 9/2004 | Wah | B23P 6/002 29/23.51 |
| 6,842,995 B2 | 1/2005 | Jones et al. | |
| 6,906,808 B2 * | 6/2005 | Trantow | G01B 5/205 356/601 |
| 6,910,278 B2 | 6/2005 | Holder | |
| 7,024,787 B2 | 4/2006 | Varsell et al. | |
| 7,328,496 B2 | 2/2008 | Powers et al. | |
| 7,337,520 B2 | 3/2008 | Jones et al. | |
| 7,412,780 B2 | 8/2008 | Holder | |
| 8,037,768 B2 | 10/2011 | Ichiryu | |
| 8,140,308 B2 | 3/2012 | Menuey | |
| 9,003,670 B2 * | 4/2015 | Romanelli | G01B 5/008 33/502 |
| 9,109,873 B1 * | 8/2015 | Lewis | G01B 3/20 |
| 9,145,792 B2 * | 9/2015 | Hunt | F01D 5/005 |
| 9,542,739 B1 * | 1/2017 | Salm | G01B 21/16 |
| 2005/0268461 A1 | 12/2005 | Ouellette et al. | |
| 2008/0247636 A1 * | 10/2008 | Davis | G06T 19/00 382/152 |
| 2009/0064520 A1 | 3/2009 | Sherlock et al. | |
| 2009/0164037 A1 * | 6/2009 | Menuey | F01D 5/225 700/103 |
| 2015/0308284 A1 * | 10/2015 | Salm | F01D 21/003 73/865.8 |

FOREIGN PATENT DOCUMENTS

| | | |
|---|---|---|
| DE | 2359227 | 6/1974 |
| DE | 2317210 | 10/1974 |
| EP | 1731717 A2 | 12/2006 |
| EP | 2075721 A1 | 7/2009 |
| FR | 2984788 A1 | 6/2013 |
| KR | 20080069306 A | 7/2008 |

OTHER PUBLICATIONS

Li et al, Aviation Blade Inspection Based on Optical Measurement, ICIRA 2013, Part II, LNAI 8103, pp. 555-568, 2013.*
EP Search Report for EP Application No. 16183799.2 dated Jan. 9, 2017, 8 pages.

* cited by examiner

VIRTUAL BLADE INSPECTION

BACKGROUND OF THE INVENTION

The disclosure relates generally to machine inspection, and more particularly, to a virtual blade inspection including, for example, axial, radial and/or twist deformation.

Blades are used to generate power from a flow of a working fluid in devices such as a turbomachine. In particular, a number of blades may be coupled to a rotor to impart rotational motion to the rotor from a flow of a working fluid thereover. Blades are initially shaped based on ideal models that create highly efficient blades. Each blade may include a shroud at an outer end thereof that includes a hard face that interacts with a mating hard surface of an adjacent blade's shroud. Hard faces are parts of the shroud that include wear material and come into contact with one another at a base load to dampen vibration. During turbine engine operation, shrouded turbine blades are subject to high amounts of distortion and twist. A contact gap between two adjacent blades is critical to ensure bucket engagement during operation. As the blades wear, the contact gap between two adjacent blades increases resulting in inadequate blade engagement. Consequently, blade hard faces often require restoration during periodic repair processes.

After repair, an inspection is performed in order to ensure the blades have been properly restored. As part of the inspection, all of the blades of a particular stage are positioned in place on a rotor wheel by axially sliding the blades into place on mating couplings on the rotor wheel. The number of blades may vary depending on the blade stage, but is typically a relatively large number, e.g., 92, 100, etc. At this point, shims having a known size are placed between each adjacent pair of blade shrouds interacting hard faces. The cumulative dimension of the shims provides a measure of the cumulative dimension of all of the contact gaps between hard faces of the rotor wheel. A cumulative contact gap that is too large indicates unsuitability of the blades for continued use. In addition, an inability to place the shims into place between certain adjacent blade shrouds indicates that one or more blades may be too twisted for use, i.e., there is no contact gap between adjacent shroud hard faces. Further, a maximum allowable gap check may also be performed during the inspection. Once the inspection is complete, the blades are removed for shipment and installing at a site. This inspection process poses a challenge in that the loading of the blades onto a rotor wheel, shimming all of the contact gaps, measuring the contact gaps/shims and removing all of blades is very labor intensive and time consuming.

The current process also does not address other structural deformations such as axial deformation. Also, radial deformation can lead to the overlay of shrouds within a wheel, causing binding referred to as 'shingling'.

BRIEF DESCRIPTION OF THE INVENTION

A first aspect of the disclosure provides a computerized method of virtually inspecting contact gaps of a blade stage, the blade stage having known dimensions, the method comprising: in a computer system: extracting a geometric location data of a hard face plane of each shroud from a three-dimensional model of a shroud of each blade of the blade stage created by digitizing using a digitizing device; generating a three-dimensional virtual rendering of the shrouds of the blade stage based on the geometric location data and the known dimensions of the blade stage, the three-dimensional virtual rendering including a rendering of contact gaps between adjacent shrouds; and inspecting the blade stage using the three-dimensional virtual rendering.

A second aspect of the disclosure provides a system for virtually inspecting contact gaps of a blade stage, the blade stage having known dimensions, the system comprising: a computer system including at least one module configured to perform the following steps: extracting a geometric location data of a hard face plane of each shroud from a three-dimensional model of a shroud of each blade of the blade stage created by digitizing using a digitizing device; generating a three-dimensional virtual rendering of the shrouds of the blade stage based on the geometric location data and the known dimensions of the blade stage, the three-dimensional virtual rendering including a rendering of contact gaps between adjacent shrouds; and inspecting the blade stage using the three-dimensional virtual rendering.

A third aspect of the disclosure provides a system for virtually inspecting contact gaps of a blade stage, the blade stage having known dimensions, the system comprising: a digitizing device for obtaining a three-dimensional model of a shroud of each blade of the blade stage; a computer system including at least one module configured to perform the following steps: extracting a geometric location data of a hard place plane of each shroud from the three-dimensional model, the extracting including identifying an x, y and z coordinate of each hard face plane in space, and identifying an angular orientation of each hard face plane in space; generating a three-dimensional virtual rendering of the shrouds of the blade stage based on the geometric location data and the known dimensions of the blade stage, the three-dimensional virtual rendering including a rendering of contact gaps between adjacent shrouds, the generating including calculating a unit normal vector to each hard face plane, radially positioning each hard face plane relative to a common axis based on a shroud radius of the blade stage, and circumferentially positioning each hard face plane about the common axis using a spacing depending on the number of blades in the blade stage; and inspecting the blade stage using the three-dimensional virtual rendering by at least one of: a) expanding each hard face plane in the unit normal vector direction, and identifying interference between adjacent shrouds in response to an expanded hard face planes of adjacent shrouds intersecting; and b) measuring a contact gap between hard face planes of each pair of adjacent blades in the three-dimensional virtual rendering, and determining whether at least one contact gap parameter exceeds a respective threshold.

A fourth aspect includes a computerized method of virtually inspecting shrouds of a blade stage, the blade stage having known dimensions, the method comprising: in a computer system: extracting a geometric location data of a plurality of reference points of each shroud from a three-dimensional model of a shroud of each blade of the blade stage created by digitizing using a digitizing device; generating a three-dimensional virtual rendering of the shrouds of the blade stage based on the geometric location data and the known dimensions of the blade stage, the three-dimensional virtual rendering including a rendering of the plurality of reference points of each shroud, wherein the generating includes: radially positioning each shroud relative to a common axis based on a shroud radius of the blade stage, and circumferentially positioning each shroud about the common axis using a spacing depending on the number of blades in the blade stage; and inspecting the blade stage using the three-dimensional virtual rendering.

A fifth aspect relates to a system for virtually inspecting a blade stage, the blade stage having known dimensions, the system comprising: a computer system including at least one module configured to perform the following steps: extracting a geometric location data of a plurality of reference points of each shroud from a three-dimensional model of a shroud of each blade of the blade stage created by digitizing using a digitizing device; generating a three-dimensional virtual rendering of the shrouds of the blade stage based on the geometric location data and the known dimensions of the blade stage, the three-dimensional virtual rendering including a rendering of the plurality of reference points of each shroud, wherein the generating includes: radially positioning each shroud relative to a common axis based on a shroud radius of the blade stage, and circumferentially positioning each shroud about the common axis using a spacing depending on the number of blades in the blade stage; and inspecting the blade stage using the three-dimensional virtual rendering.

A sixth aspect includes a system for virtually inspecting a blade stage, the blade stage having known dimensions, the system comprising: a digitizing device for obtaining a three-dimensional model of at least a shroud of each blade of the blade stage; a computer system including at least one module configured to perform the following steps: extracting a geometric location data of a plurality of reference points of each shroud from a three-dimensional model of a shroud of each blade of the blade stage created by digitizing using a digitizing device; generating a three-dimensional virtual rendering of the shrouds of the blade stage based on the geometric location data and the known dimensions of the blade stage, the three-dimensional virtual rendering including a rendering of the plurality of reference points of each shroud, wherein the generating includes: radially positioning each shroud relative to a common axis based on a shroud radius of the blade stage, and circumferentially positioning each shroud about the common axis using a spacing depending on the number of blades in the blade stage, inspecting the blade stage using the three-dimensional virtual rendering by identifying at least one of an axial deformation, a radial deformation, a twist deformation, and a contact gap violation; and modifying at least one blade to at least reduce the at least one of the axial deformation, the radial deformation, the twist deformation, and the contact gap violation.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, the disclosure provides for virtual blade inspection. Embodiments of the disclosure may include a computerized method and a system for virtually inspecting contact gaps of a blade stage of, for example, a turbomachine. The blade stage being inspected has known dimensions, i.e., outer radius, circumference, inner radius, number of blades, etc. In other embodiments, the inspection system may employ a number of vertical reference points on a hard face plane to inspect contact gaps. In further embodiments, the inspection system may inspect contact gaps, and/or a variety of deformations such as an axial, radial and/or twist deformation.

Figure 1:
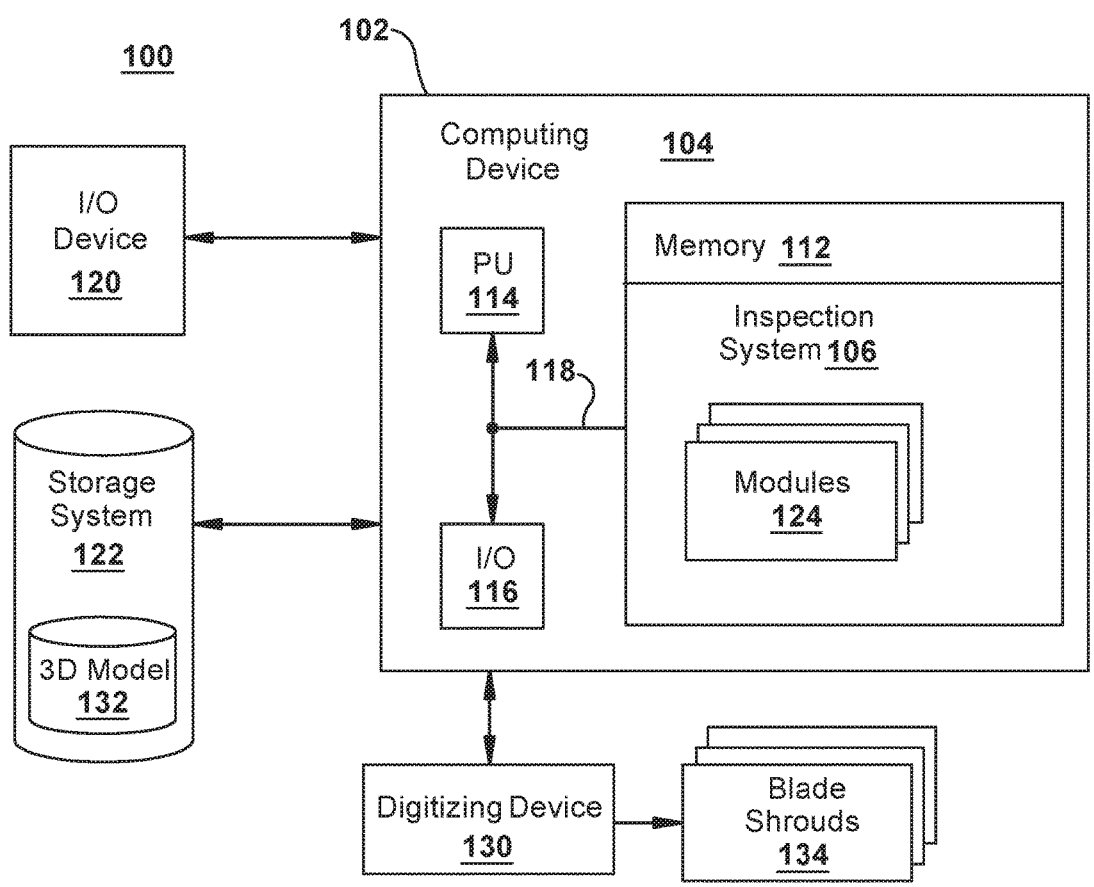
FIG. 1 shows a block diagram of an illustrative environment of an inspection system for virtually inspecting a blade stage according to embodiments of the disclosure.

Referring now to FIG. 1, a block diagram of an illustrative environment 100 for virtually inspecting a blade stage according to embodiments of the disclosure is shown. To this extent, environment 100 includes a computer infrastructure 102 that can perform the various process steps described herein for virtually inspecting a blade stage. In particular, computer infrastructure 102 is shown including a computing device or system 104 that comprises an inspection system 106, which enables computing device 104 to virtually inspect a blade stage by performing the process steps of the disclosure.

Computing device 104 is shown including a memory 112, a processor (PU) 114, an input/output (I/O) interface 116, and a bus 118. Further, computing device 104 is shown in communication with an external I/O device/resource 120 and a storage system 122. As is known in the art, in general, processor 114 executes computer program code, such as inspection system 106, that is stored in memory 112 and/or storage system 122. While executing computer program code, processor 114 can read and/or write data, such as digitized three-dimensional models of a shroud of a blade, to/from memory 112, storage system 122, and/or I/O interface 116. Bus 118 provides a communications link between each of the components in computing device 104. I/O device 118 can comprise any device that enables a user to interact with computing device 104 or any device that enables computing device 104 to communicate with one or more other computing devices. Input/output devices (including but not limited to keyboards, displays, pointing devices, etc.) can be coupled to the system either directly or through intervening I/O controllers.

In any event, computing device 104 can comprise any general purpose computing article of manufacture capable of executing computer program code installed by a user (e.g., a personal computer, server, handheld device, etc.). However, it is understood that computing device 104 and inspection system 106 are only representative of various possible equivalent computing devices that may perform the various process steps of the disclosure. To this extent, in other embodiments, computing device 104 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively.

Similarly, computer infrastructure 102 is only illustrative of various types of computer infrastructures for implementing the disclosure. For example, in one embodiment, computer infrastructure 102 comprises two or more computing devices (e.g., a server cluster) that communicate over any type of wired and/or wireless communications link, such as a network, a shared memory, or the like, to perform the various process steps of the disclosure. When the communications link comprises a network, the network can comprise any combination of one or more types of networks (e.g., the Internet, a wide area network, a local area network, a virtual private network, etc.). Network adapters may also be coupled to the system to enable the data processing system to become coupled to other data processing systems or remote printers or storage devices through intervening private or public networks. Modems, cable modem and Ethernet cards are just a few of the currently available types of network adapters. Regardless, communications between the computing devices may utilize any combination of various types of transmission techniques.

As previously mentioned and discussed further below, inspection system 106 enables computing infrastructure 102 to virtually inspect a blade stage of, for example, a turbomachine. To this extent, inspection system 106 is shown including a number of modules 124. Operation of each of these modules is generally discussed herein. However, it is understood that some of the various systems shown in FIG. 1 can be implemented independently, combined, and/or stored in memory for one or more separate computing devices that are included in computer infrastructure 102. Further, it is understood that some of the systems and/or functionality may not be implemented, or additional systems and/or functionality may be included as part of environment 100.

Environment 100 may also include a digitizing device 130 for creating a three-dimensional (3D) model 132 (shown in storage system 122) of a shroud 134 of each blade of the blade stage by digitizing. As used herein, "digitizing" includes any now known or later developed method of creating three-dimensional coordinates of at least a portion of a part. Digitizing device 130 may include a mechanical apparatus such as those that employ a tracing tip, gauges or indicators, or articulated arms or may include an optical system such as those that employ photogrammetry techniques or a laser scanner or tracker or displacement sensors or other structured light or camera. In any event, the digitizing creates a large number of coordinates in a three-dimensional space such that 3D model 132 takes the form of a mesh on a display. Each shroud 134 may be digitized in a disassembled state apart from a respective rotor wheel, and independent of other shrouds. Any appropriate fixture may be employed for supporting and holding each shroud in a uniform manner during the digitizing. While FIG. 1 is illustrated including a digitizing device 130 for digitizing shrouds 134, it is understood that embodiments of the disclosure call for "obtaining" a three-dimensional model of a shroud of each blade of the blade stage by digitizing using a digitizing device. Consequently, it is understood that embodiments of the method may employ a 3D model 132 that is not directly generated but obtained from a third party that performs the digitization. When the data is not generated by digitizing device 130 directly, it is understood that another system/component can be implemented apart from the system/component shown, which generates 3D model 132 and provides it to inspection system 106/or stores the data for access by the system. In this regard, various systems and components as described may "obtain" data such as 3D model 132 of a shroud, etc. It is understood that the corresponding data can be obtained using any solution. For example, the corresponding system/component can retrieve the data from one or more data stores (e.g., a database), or receive the data from another system/component, and/or the like.

Figure 2:
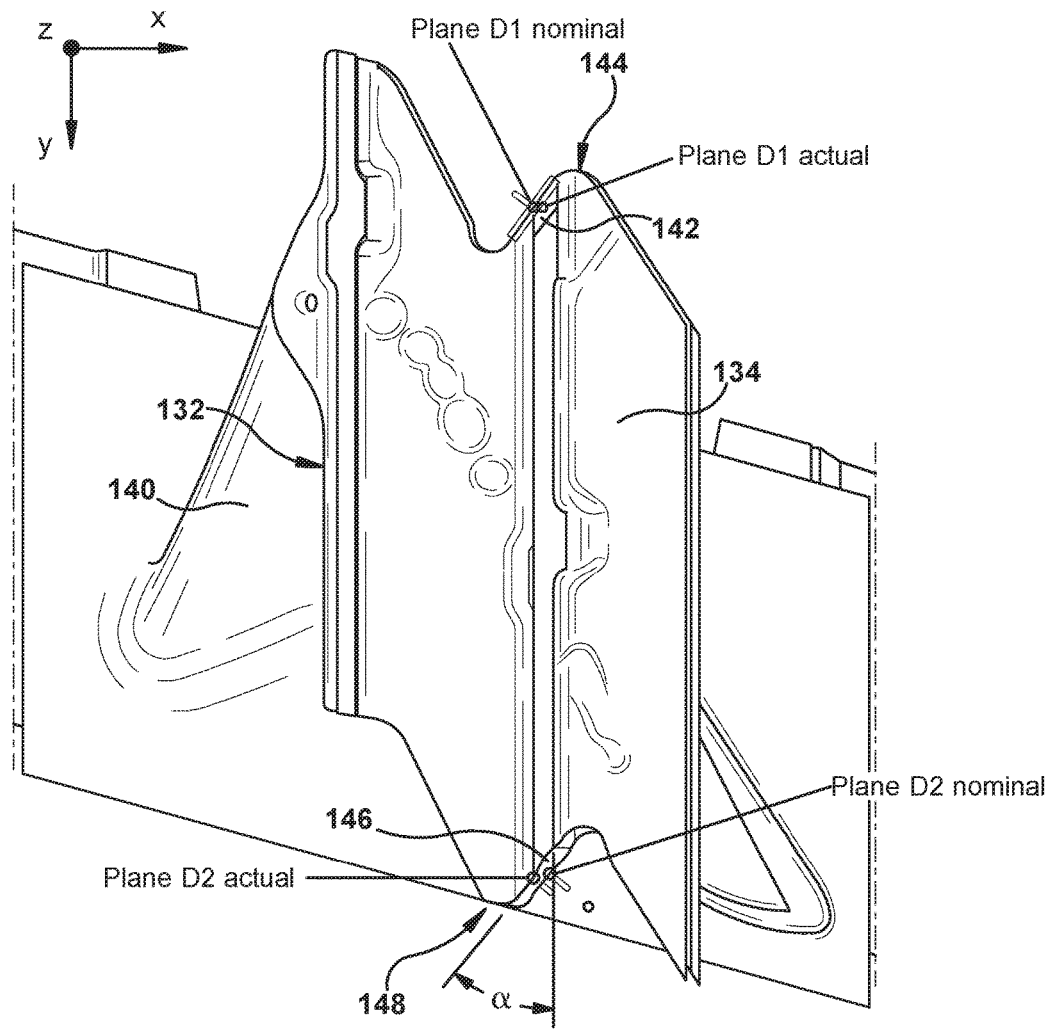
FIG. 2 shows a top view of a three-dimensional model of a shroud of a blade according to embodiments of the disclosure.
Figure 3:
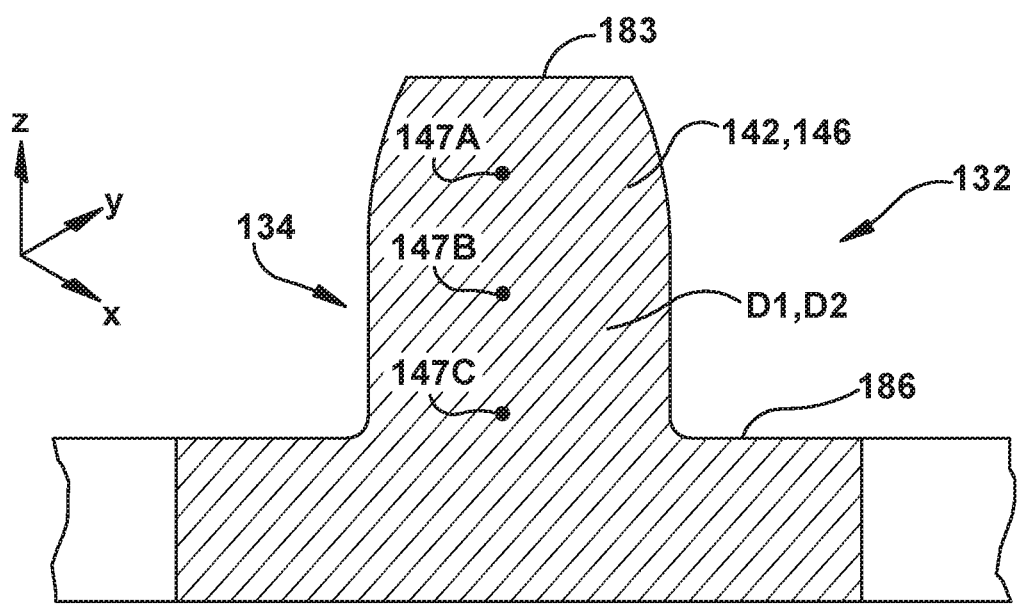
FIG. 3 shows an enlarged end view of a three dimensional virtual rendering of a hard face plane of a shroud according to embodiments of the disclosure.

Referring to FIG. 2, an illustrative 3D model 132 of shroud 134 of a blade 140 is illustrated. 3D model 132 illustrates a first hard face plane D1 of a hard face 142 at a first circumferential end 144 of shroud 134, and a second hard face plane D2 of a second hard face 146 at an opposing, second circumferential end 148. As understood in the art, blade 140 is slid into a rotor wheel in an axial direction x that parallels a rotor axis (not shown), and adjacent blades 140 mate along hard faces 142 and 146. 3D model 132, as noted, may be obtained using digitizing device 130 (FIG. 1) that may include a mechanical apparatus such as those that employ a tracing tip, or may include an optical system such as those that employ a laser scanner or other structured light. FIG. 3 shows a rendering from a digitizing device in the form of a structured light device created by a 3D light scanner such as but not limited to: an ATOS industrial 3D scanner available from GOM GmbH, or a Steinbichler COMET L3D scanner available from Carl Zeiss Optotechnik GmbH Continuing with FIGS. 2-7, inspection system 106 (FIG. 1) extracts geometric location data of a plurality of reference points of each shroud in 3D model 132 of a shroud 134 of each blade 140 of the blade stage. In FIGS. 2-7, the x axis extends parallel to a rotor axis (not shown), the y axis extends in a first radial direction laterally from the rotor axis, and the z axis extends in a second radial direction vertically from the rotor axis (see legends).

In one embodiment, as shown in FIG. 2, the geometric location data may include reference points of hard face plane(s) D1, D2 of each shroud 134 from 3D model 132. The extracting of the geometric location data may include, for example, identifying an x, y and z coordinate of each hard face plane D1, D2 in space. Consequently, in FIG. 2, each hard face plane D1, D2 includes a number of data points in three-dimensional space such that a best fit plane can be ascertained. In another embodiment, shown in the enlarged end view of FIG. 3 of hard faces 142, 146, inspection system 106 may extract the geometric location data by identifying an x, y and z coordinate of a plurality of vertical reference points, e.g., 147A-C, along a hard face 142, 146 (hard face planes D1, D2) of each shroud 134 in space. As each blade 134 is fixed in a holder or support in an identical fashion to every other blade during digitizing, the x, y, z coordinates share a common origin as a reference. The extracting may also include identifying a compound angular orientation α (FIG. 2) of each hard face plane D1, D2 in space (only one shown). The extraction thus provides geometric location data of each hard face plane D1, D2 relative to a common reference point.

Figure 4:
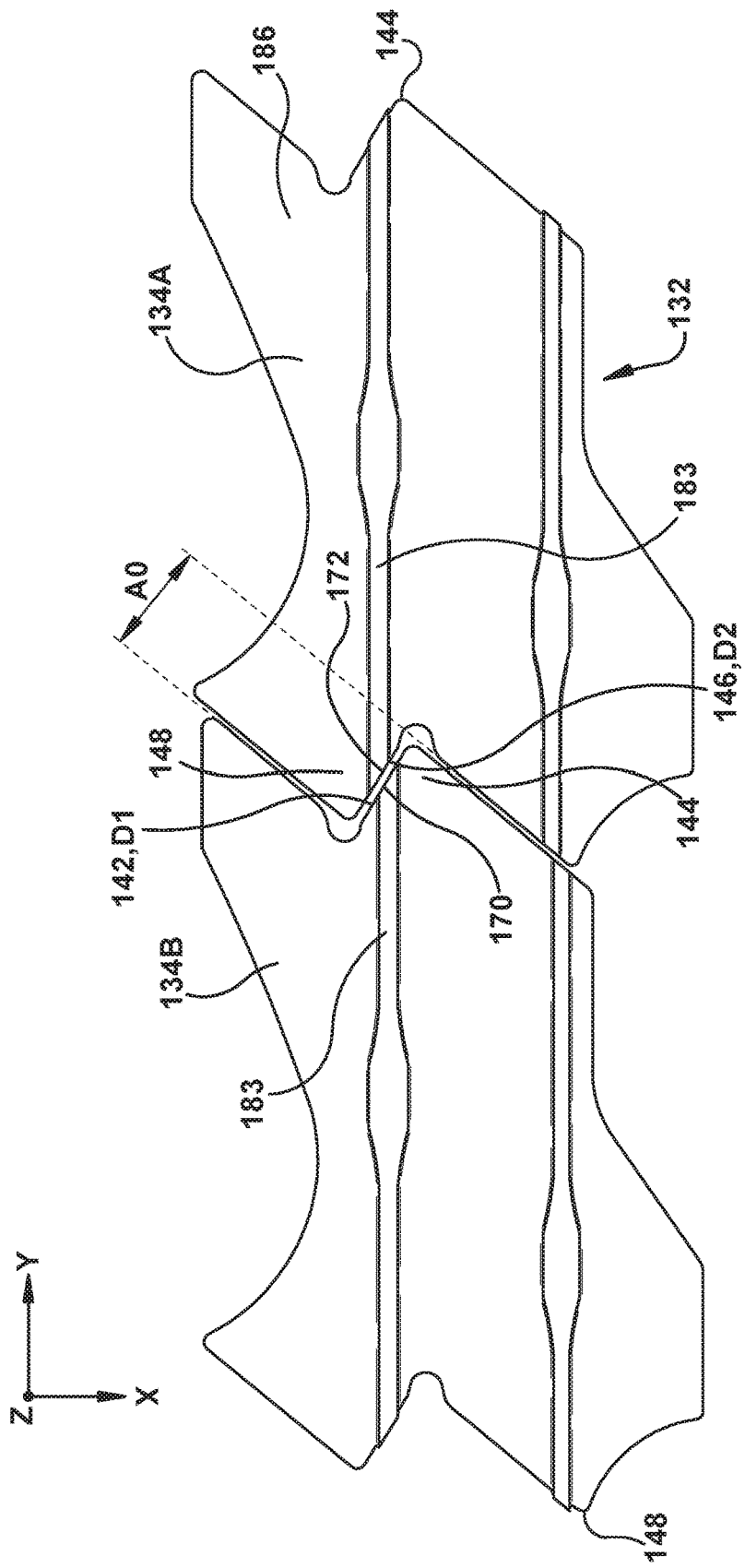
FIG. 4 shows a top view of a three dimensional virtual rendering of a pair of adjacent shrouds according to embodiments of the disclosure.
Figure 5:
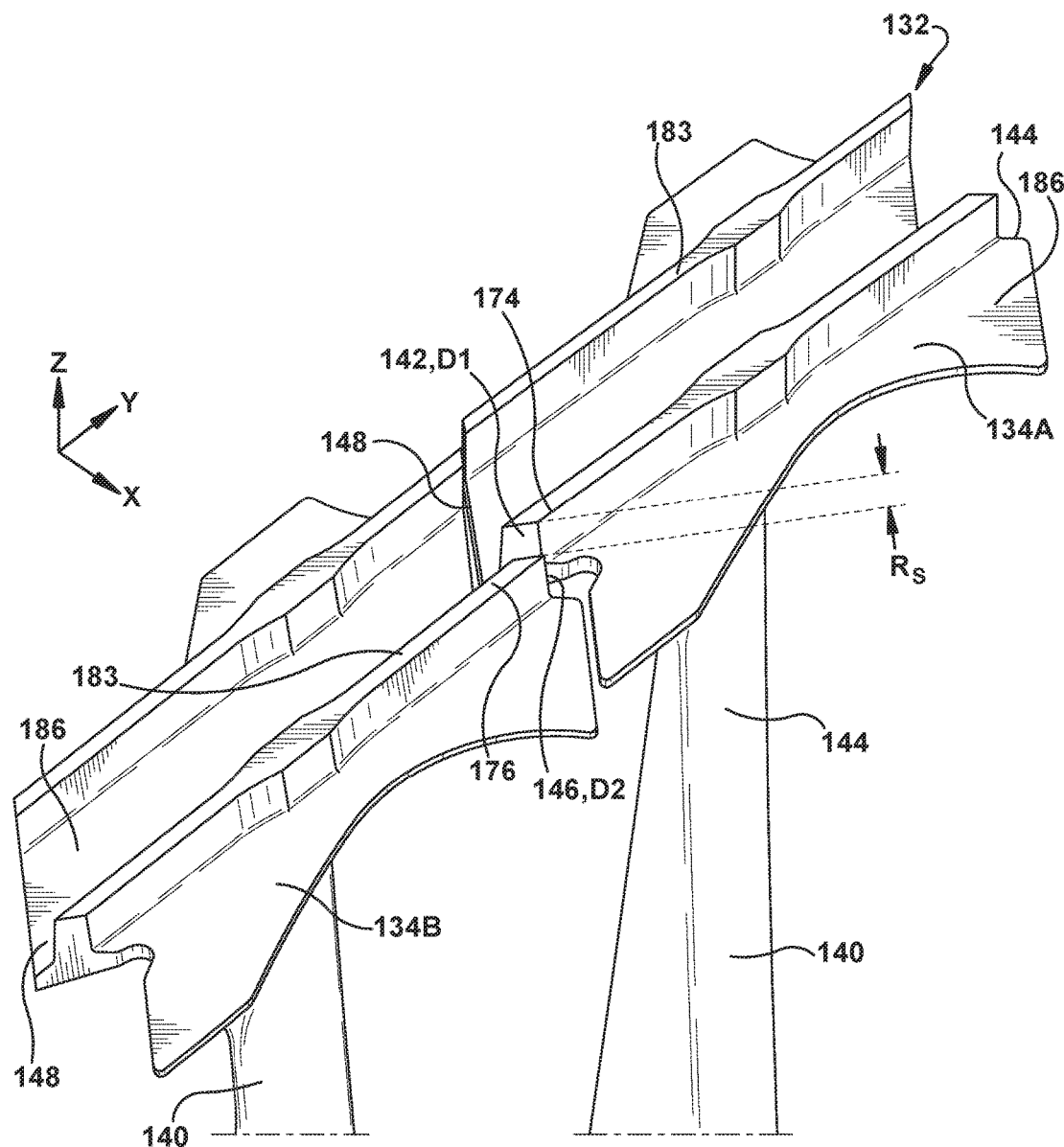
FIG. 5 shows a top perspective view of a three dimensional virtual rendering of a pair of adjacent shrouds according to embodiments of the disclosure.
Figure 6:
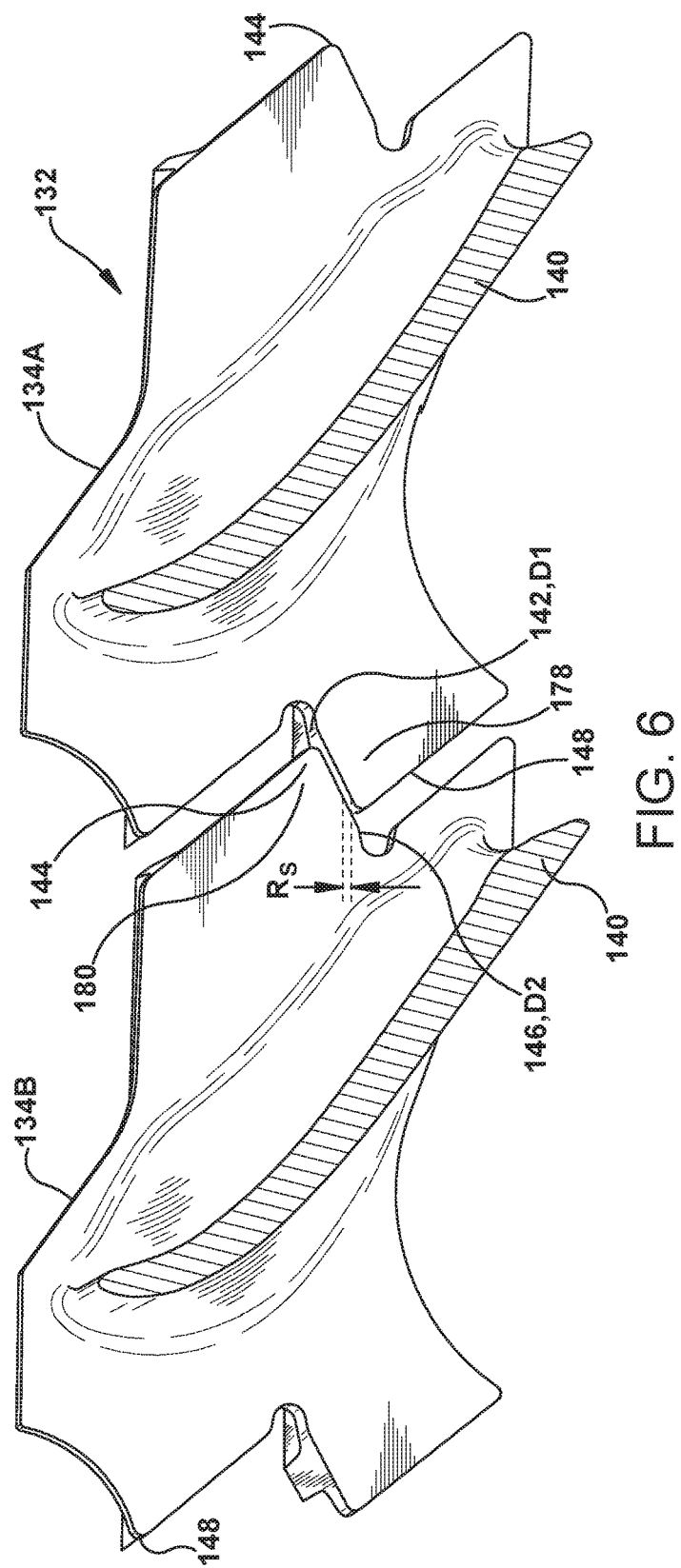
FIG. 6 shows a bottom perspective view of a three dimensional virtual rendering of a pair of adjacent shrouds according to embodiments of the disclosure.
Figure 7:
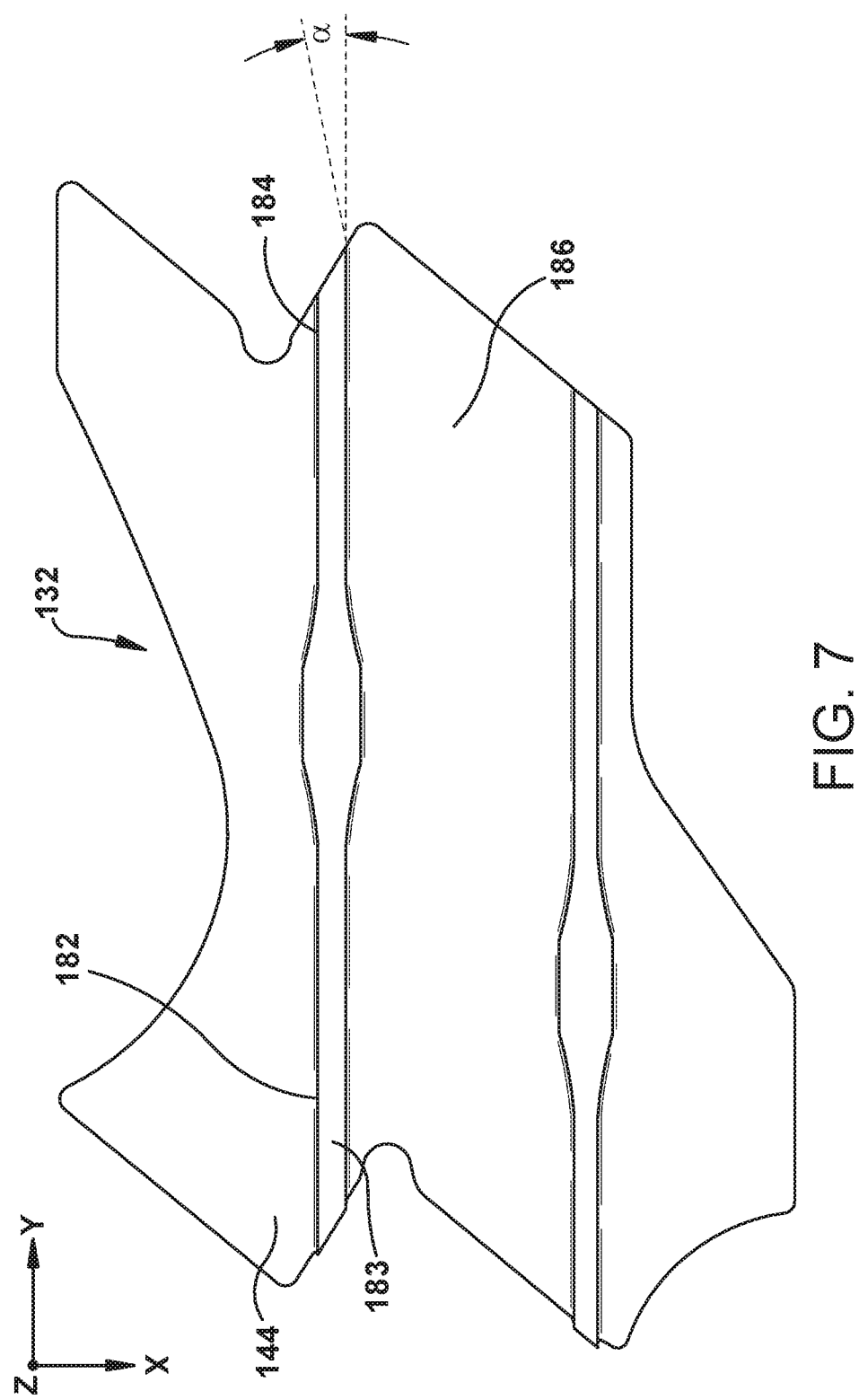
FIG. 7 shows a top view of a three-dimensional model of a shroud of a blade according to embodiments of the disclosure.

Referring to FIGS. 4-7, in other embodiments in which, for example, deformations are identified, only specific reference points may be extracted. For example, as shown in FIG. 4, for use in identifying an axial deformation as will be described herein, inspection system 106 may extract the geometric location data by identifying x coordinates of a pair of corresponding axial reference points 170, 172 of hard face planes D1, D2 (of hard faces 142, 146, respectively) for each pair of adjacent shrouds 134A, 134B in space, respectively. The x coordinates may be the same as or different than those extracted relative to FIG. 2. In another example, shown FIGS. 5 and 6, for use in identifying a radial deformation as will be described herein, inspection system 106 may extract the geometric location data by identifying, for each shroud 134A, 134B in space, a z coordinate of a selected radial point. As shown in FIG. 5, the selected radial point (z coordinate) may be an outermost radial point 174, 176 of a hard face plane D1, D2, respectively, or as shown in FIG. 6, the selected radial point (z coordinate) may be an innermost radial point 178, 180 of hard face plane D1, D2, respectively. In FIG. 5, outermost radial point is on an outermost surface of a half-rib 183 extending from an outer facing surface 186 of shroud 134A, 134B. The z coordinates may be the same as or different than those extracted relative to FIG. 2. In yet another example, as shown in FIG. 7, inspection system 106 may extract the geometric location data by identifying a pair of x coordinate reference points 182, 184 for each shroud 134 in space. In this example, the x-coordinate reference points 182, 184 are on half rib 183 extending from an outer facing surface 186 of shroud 134. The use of each embodiment of extraction of reference point(s) will be described in greater detail herein.

Figure 8:
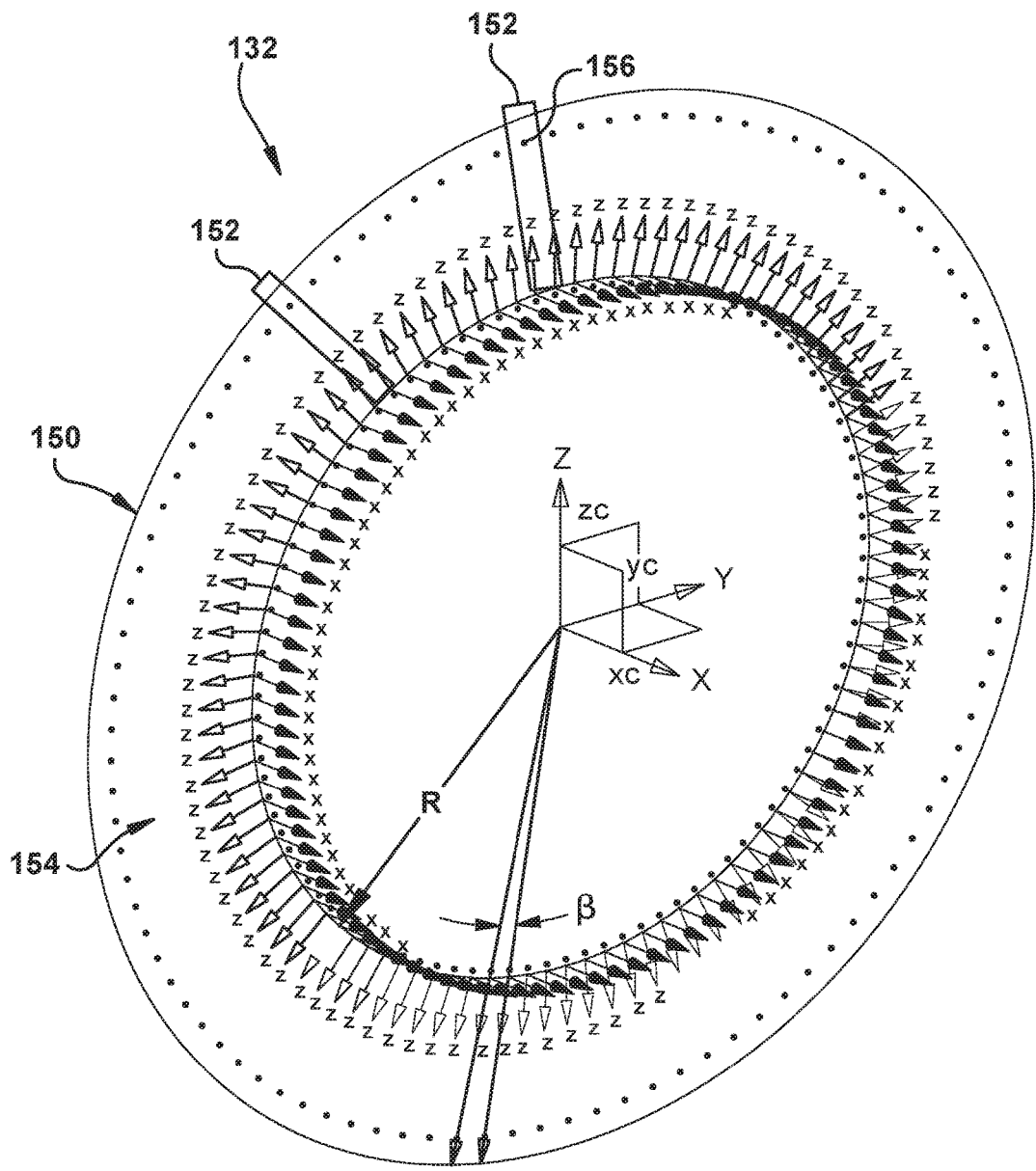
FIG. 8 shows a three dimensional virtual rendering of a blade stage according to embodiments of the disclosure.

As shown in FIG. 8, inspection system 106 (FIG. 1) generates a three-dimensional (3D) virtual rendering 150 of shrouds 152 (two denoted with boxes) of blade stage 154 based on the geometric location data (FIG. 2) of each blade, and the known dimensions of the blade stage 154. The generating of 3D virtual rendering 150 may include radially positioning each shroud 152 relative to a common axis (e.g., y axis) based on a shroud radius R of blade stage 154. In one embodiment, the rendering may include radially positioning at least each hard face plane D1, D2 (one pair collectively referenced as 156 in FIG. 8, but produced for each blade) relative to a common axis (e.g., y axis) based on a shroud radius R of blade stage 154. Shroud radius R is a known dimension of a blade stage 154 upon which a particular z axis offset for shrouds 152 (blades of blade stage 154) can be positioned in the 3D virtual rendering 150, e.g., in FIG. 8 from X, Y, Z coordinate at center to working x, y, z coordinates. In addition, the generating may include circumferentially positioning each hard face plane D1, D2 (FIG. 4) about common axis (e.g., y axis) using a spacing depending on the number of blades in blade stage 150. The circumferential positioning may include assigning each blade 152 a clocking angle β equal to 360° divided by the number of blades in blade stage 154. In the example shown, 92 blades are provided, so the clocking angle β or circumferential spacing is 3.91°; other angles would be used for different number of blades. As used herein, "rendering" has been shown as creating a virtual image for the purposes of description. It is emphasized, however, that rendering does not necessarily require creating an image, and can include any electronic representation.

Figure 9:
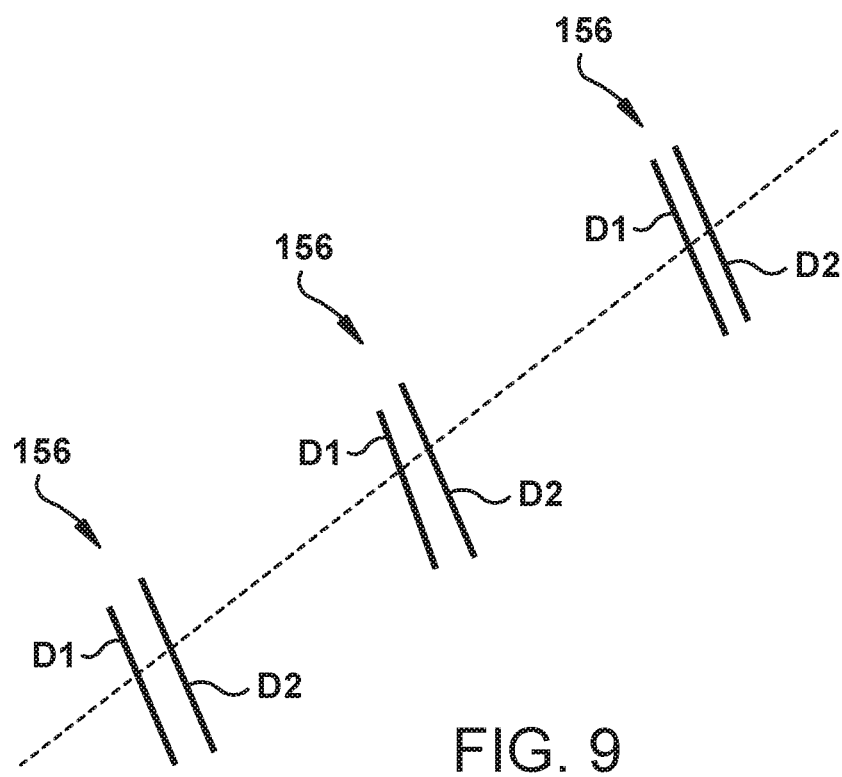
FIG. 9 shows an enlarged plan view of a number of shroud ends according to embodiments of the disclosure.

FIG. 9 shows a radially inward and enlarged view of examples of expanded hard face planes D1, D2, as will be described herein. Expanded hard face planes are also illustrated collectively for each shroud 152 as reference 156 in FIG. 8.

Figure 10:
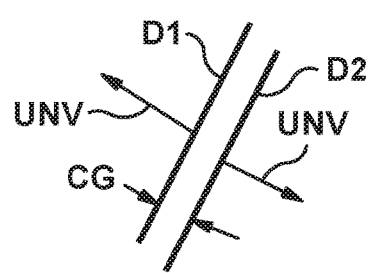
FIGS. 10-13 show enlarged views of two examples of shroud ends undergoing inspection according to embodiments of the disclosure.
Figure 11:
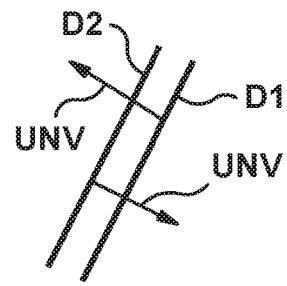

FIGS. 10 and 11 show two examples of enlarged schematic view of hard face planes D1, D2—as are illustrated collectively for each shroud 152 as reference 156 in FIGS. 8 and 9. In the examples, hard face plane D1 is a leading edge plane and hard face plane D2 is a trailing edge plane. FIG. 10 illustrates a situation where a contact gap CG exists, and FIG. 11 illustrates an interference situation where no gap exists, which is one example of a contact gap violation as defined elsewhere herein. Thus, 3D virtual rendering 150 (FIG. 3) includes a rendering of contact gaps CG, where present, between adjacent shrouds for all of shrouds 152 (FIG. 3) in blade stage 154 (FIG. 3). Consequently, 3D virtual rendering 150 provides a virtual model of blade stage 154 without having to actually put each blade into position on a rotor wheel, thus reducing the time and labor necessary to evaluate shroud repair work. As also shown in FIGS. 10 and 11, the generating may also include calculating a unit normal vector (UNV) to each hard face plane D1, D2, which indicates a direction perpendicular to each plane. The function of the unit normal vectors will be described herein.

Inspection system 106 may also perform a variety of inspection steps of blade stage 154 (FIG. 8), including particular (virtual) shrouds 154 thereof, using 3D virtual rendering 150 (FIG. 8). In particular, inspection system 106 can identify, as will be described, at least one of an axial deformation, a radial deformation, a twist deformation, and a contact gap violation.

Figure 12:
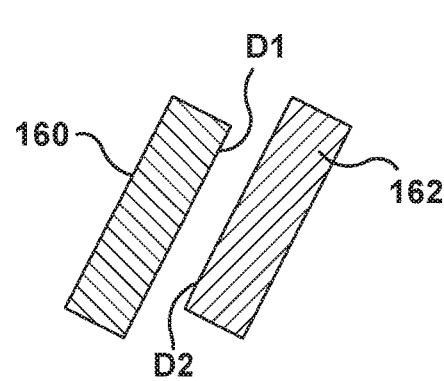
Figure 13:
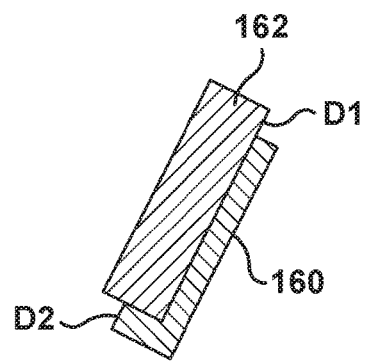

In one embodiment, with regard to identifying a contact gap violation, as shown in FIGS. 12 and 13, the inspecting may include: expanding each hard face plane D1, D2 in the unit normal vector (UNV) direction. A "contact gap violation" may include any situation where the minimum or maximum contact gap is not as specified, e.g., where an interference exists or too large of a gap exists. As shown in FIGS. 12 and 13, the expansion results in a rectangular shape 160, 162 projecting perpendicularly from each respective plane D1, D2, respectively. Based on the expansion, inspection system 106 can identify interference, as shown in FIG. 13, between adjacent shrouds in response to the expanded hard face planes 160, 162 of adjacent shrouds intersecting, i.e., a contact gap violation. In contrast, in FIG. 12, no interference is identified because expanded hard face planes 160, 162 of hard face planes D1, D2, respectively, do not intersect. The inspection may occur for each pair of adjacent shrouds 152 (FIG. 8) in 3D virtual rendering 150 (FIG. 8), thus eliminating the need to physically check each contact gap. Where a plurality of vertical reference points 147A-C (FIG. 4) are extracted, the above-described process can be repeated at each vertical point, thus checking for various contact gap violations (i.e., intersection) along a vertical extent of hard face planes D1, D2.

In another embodiment, inspection system 106 may measure a contact gap CG (FIG. 10) between hard face planes D1, D2 of each pair of adjacent blades 152 (FIG. 8) in 3D virtual rendering 150 (FIG. 8). The measurements may be used in a number of ways. In one embodiment, inspection system 106 may use the measured contact gaps to identify a minimum contact gap amongst the contact gaps, and then determine whether the minimum contact gap exceeds a threshold. For example, if no individual contact gap can be less than a certain dimension, this process would identify which pair(s) of shrouds 152 were out of compliance. Similarly, inspection system 106 may use the measured contact gaps to identify a maximum contact gap amongst the contact gaps, and then determine whether the maximum contact gap exceeds a threshold. For example, if no individual contact gap can be greater than a certain dimension, this process would identify which pair(s) of shrouds 152 were out of compliance.

In another embodiment, where plurality of vertical reference points, 147A-C (FIG. 4), on each hard face plane D1, D2 are identified, inspection system 106 may measure a contact gap between hard face planes D1, D2 of each pair of adjacent blades in the three-dimensional virtual rendering at each of plurality of vertical reference points, 147A-C (FIG. 4). That is, for each pair of adjacent shrouds 134A, 134B, a plurality of contact gaps are measured. In this case, a minimum (or maximum) contact gap amongst the contact gaps at each of the plurality of vertical reference points may be identified, and a contact gap violation may be identified, as noted herein, by determining whether the minimum (or maximum) contact gap exceeds a threshold. As noted, a contact gap violation may include any situation where the minimum or maximum contact gap is not as specified. Further, in another embodiment, regardless of whether a single or many contact gaps are measured, inspection system 106 may calculate a cumulative contact gap by summing the contact gaps. That is, for all of the shroud pairs, the sum of the contact gaps may be summed. Where more than one contact gap for each pair is identified, the summing may be across those contact gaps at the same vertical position (e.g., for all gaps at point 147A), or may be cumulative across all contact gaps (e.g., for all gaps at points 147A-C). In any event, the cumulative contact gap may be used determine whether the cumulative contact gap exceeds a threshold, which may indicate a repair or modification is necessary.

Angular orientation of hard face planes D1, D2 and other features of shrouds 134 can also be evaluated using 3D virtual rendering 150 (FIG. 8). In one embodiment, with reference to FIG. 7, based on identified x-coordinates 182, 184, inspection system 106 may measure a twist amount $\gamma$ of each shroud 134 in space by measuring a shift in space of each of the pair of x coordinates 182, 184 thereof relative to an expected location of each x coordinate (using basic geometric calculations). That is, by measuring a distance each x coordinate reference point 182, 184 has moved from an expected location (stored in memory of system 100), a twist amount $\gamma$ of shroud 134 can be identified. Based on one or more twist amounts $\gamma$ individually exceeding a threshold, e.g., 1°, inspection system 106 can determine a twist deformation exists, necessitating replacement or repair of one or more shrouds 134 including the twists. Although shroud 134 in FIG. 7 has been shown to have twisted in a particular direction, e.g., counterclockwise, the twist can occur in the other direction, i.e., clockwise.

In another embodiment, axial and/or radial deformations can be identified using 3D virtual rendering 150 (FIG. 8).

Referring to FIG. 4, an axial deformation may include a lack of overlap or too little overlap of hard face planes D1, D2 of pairs of adjacent shrouds 134A, 134B in a generally axial (x) direction. The axial direction, as illustrated, may not be perfectly aligned with the x axis. In order to identify an axial deformation, inspection system 106 may measure an axial overlap (AO) between hard face planes D1, D2 of each pair of adjacent blades 134A, 134B in 3D virtual rendering 132 based on the x coordinates of the pair of corresponding axial reference points 170, 172. That is, knowing the extracted position of x coordinates at point 170 on hard face 142 and point 172 on hard face 144, an axial overlap (AO) can be measured using, e.g., simple geometric calculations. Once an axial overlap (AO) is known, inspection system 106 may identify an axial deformation by determining whether one or more axial overlaps individually exceed a threshold, e.g., 2 cm. In another embodiment, inspection system 106 measuring axial overlap (AO) may include calculating an axial areal overlap, i.e., a percentage of an area of each hard face plane D1, D2 that overlaps. That is, knowing points 170, 172 and an area of each hard face plane D1, D2 (e.g., shaded area in FIG. 3), inspection system 106 may calculate the amount of axial areal overlap. The areal extent of each hard face plane D1, D2 (shaded area in FIG. 3) can be determined in any consistent fashion desired by a user, e.g., that of the inverted T-shape of the plane or some sub-region thereof. Inspection system 106 can then determine an axial deformation exists by determining whether one or more axial areal overlaps exceed a threshold, e.g., 50%.

Referring to FIGS. 5 and 6, a radial deformation may include a lack of overlap or too little overlap of hard face planes D1, D2 of pairs of adjacent shrouds 134A, 134B in a radial (z) direction. In order to identify a radial deformation, inspection system 106 may measure a radial shift (Rs) between each pair of adjacent blades 134A, 134B in 3D virtual rendering 132 based on the x coordinates of the pair of corresponding axial reference points, i.e., either outermost radial points 174, 176 (FIG. 5) or innermost radial points 178, 180 (FIG. 6). That is, knowing the extracted position of z coordinates, e.g., at point 174 on shroud 134A and point 176 on shroud 134B, a radial shift ($R_s$) can be measured using simple geometric calculations. Once a radial shift ($R_s$) is known, inspection system 106 may identify a radial deformation by determining whether one or more radial shifts ($R_s$) (see FIG. 5) individually exceed a threshold, e.g., 1 cm. In another embodiment, inspection system 106 measuring radial shift ($R_s$) may include calculating a radial areal overlap, i.e., a percentage of each hard face plane D1, D2 area that radial overlaps. That is, knowing points 174, 176 (or 178, 180) and an area of each hard face plane D1, D2 (e.g., shaded area FIG. 3), inspection system 106 may calculate the amount of radial areal overlap. The areal extent of each hard face plane D1, D2 (FIG. 4) can be determined in any consistent fashion desired by a user. Inspection system 106 can then determine a radial deformation exists by determining whether one or more axial areal overlaps exceed a threshold, e.g., 50%.

Regardless of the form of shroud flaw identified, based on the inspecting performed by inspection system 106, an operator may modify at least one blade 140 to at least reduce the at least one of the axial deformation, the radial deformation, the twist deformation, and the contact gap violation. Any modifying of one or more blades that may be necessary can be carried out based on results from inspection system 106. The modifications may include any now known or later developed changes such as replacement, removal or addition of material of hard faces 142, 146 or other parts of shrouds 134 to modify, e.g., contact gap distances and/or angles, radial or axial positioning, twisting, etc. In addition, particular shrouds 134 may have their position changed within a particular blade stage. For example, referring to FIG. 8, a circumferential position of at least one blade within a blade stage based on the 3D virtual rendering can be changed. As understood in the art, blade stages typically undergo a moment weight balancing to ensure the blade stage is balanced weight-wise to prevent, for example, undesired vibration. Once a circumferential position of a blade has been changed (virtually) by inspection system 106, the system can ensure moment weight balancing of the revised blade stage does not exceed a (imbalance) threshold, which may vary depending on many factors such as the size of the turbine. In one non-limiting example, a particular weight balancing may range from 60 to 66 gram-millimeters. This process can be carried out by inspection system 106 verifying in a conventional manner that the blade stage does not exceed the imbalance threshold. In any event, inspection system 106 can be employed repeatedly once modifications have been made to ensure blades 140 are properly repaired and positioned before being re-used, and to achieve optimal results for any of the flaws described herein.

The herein described inspection system 106 and related methodology and software allows for characterization of various physical characteristics to improve blade engagement and reduce potential life reductions, and assists in ensuring blades assemble properly. It also eliminates the need for hard fixturing and related physical measurement techniques that are time consuming and labor intensive.

As will be appreciated by one skilled in the art, embodiments of the present disclosure may be embodied as a system, method or computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product embodied in any tangible medium of expression having computer-usable program code embodied in the medium.

Any combination of one or more non-transitory computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present disclosure is described herein with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The foregoing drawings show some of the processing associated according to several embodiments of this disclosure. In this regard, each drawing within a flow of the drawings represents a process associated with embodiments of the method described. It should also be noted that in some alternative implementations, the acts noted in the drawings or blocks may occur out of the order noted in the figure or, for example, may in fact be executed substantially concurrently or in the reverse order, depending upon the act involved. Also, one of ordinary skill in the art will recognize that additional blocks that describe the processing may be added.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A computerized method of virtually inspecting shrouds of a blade stage, the blade stage having known dimensions, the method comprising:
    in a computer system:
    extracting a geometric location data of a plurality of reference points of each shroud from a three-dimensional model of a shroud of each blade of the blade stage created by digitizing using a digitizing device;
    generating a three-dimensional virtual rendering of the shrouds of the blade stage based on the geometric location data and the known dimensions of the blade stage, the three-dimensional virtual rendering including a rendering of the plurality of reference points of each shroud, wherein the generating includes:
        radially positioning each shroud relative to a common axis based on a shroud radius of the blade stage, and
        circumferentially positioning each shroud about the common axis using a spacing depending on the number of blades in the blade stage; and
    inspecting the blade stage using the three-dimensional virtual rendering.

2. The method of claim 1, wherein the inspecting includes:
    identifying at least one of an axial deformation, a radial deformation, a twist deformation, and a contact gap violation, and
    further comprising modifying at least one blade to at least reduce the at least one of the axial deformation, the radial deformation, the twist deformation, and the contact gap violation.

3. The method of claim 1, wherein the extracting the geometric location data includes:
    identifying x coordinates of a pair of corresponding axial reference points of a hard face plane for each pair of adjacent shrouds in space; and
    wherein the inspecting includes:
    measuring an axial overlap between hard face planes of each pair of adjacent blades in the three-dimensional virtual rendering based on the x coordinates of the pair of corresponding axial reference points, and
    identifying an axial deformation by determining whether an axial overlap individually exceeds a threshold.

4. The method of claim 3, wherein the measuring the axial overlap includes calculating an axial areal overlap, and the determining includes determining whether an axial areal overlap exceeds a threshold.

5. The method of claim 1, wherein the extracting the geometric location data includes:
    identifying, for each shroud in space, a z coordinate of a selected radial point chosen from the group consisting of an outermost radial point of a hard face plane and an innermost radial point of the hard face plane; and
    wherein the inspecting includes:
    measuring a radial shift between the selected radial point of each pair of adjacent blades in the three-dimensional virtual rendering, and
    identifying a radial deformation by determining whether one or more radial shifts individually exceed a threshold.

6. The method of claim 5, wherein the measuring the radial shift includes calculating a radial areal overlap, and the determining includes determining whether a radial areal overlap individually exceeds a threshold.

7. The method of claim 1, wherein the extracting the geometric location data includes:
    identifying a pair of x coordinates for each shroud in space; and
    wherein the inspecting includes:
    measuring a twist amount of each shroud in space by measuring a shift in space of each of the pair of x coordinates thereof relative to an expected location of each x coordinate, and
    identifying a twist deformation by determining whether one or more twist amounts individually exceed a threshold.

8. The method of claim 1, wherein the extracting the geometric location data includes:
    identifying an x, y and z coordinate of a plurality of vertical reference points along a hard face plane of each shroud in space, and
    identifying an angular orientation of each hard face plane in space; and
    wherein the inspecting includes:
    measuring a contact gap between hard face planes of each pair of adjacent blades in the three-dimensional virtual rendering at each of the plurality of vertical reference points on each hard face plane,
    identifying a minimum contact gap amongst the contact gaps at each of the plurality of vertical reference points, and identifying a contact gap violation by determining whether the minimum contact gap exceeds a threshold.

9. The method of claim 1, further comprising:
based on the inspecting, changing a circumferential position of at least one blade within the blade stage within the three-dimensional virtual rendering of the shrouds of the blade stage; and
ensuring a moment weight balancing of the blade stage does not exceed a threshold.

10. A system for virtually inspecting a blade stage, the blade stage having known dimensions, the system comprising:
a computer system including a processor connected to a memory and at least one module, the module configured to perform the following processes:
extracting a geometric location data of a plurality of reference points of each shroud from a three-dimensional model of a shroud of each blade of the blade stage created by digitizing using a digitizing device;
generating a three-dimensional virtual rendering of the shrouds of the blade stage based on the geometric location data and the known dimensions of the blade stage, the three-dimensional virtual rendering including a rendering of the plurality of reference points of each shroud, wherein the generating includes:
radially positioning each shroud relative to a common axis based on a shroud radius of the blade stage, and
circumferentially positioning each shroud about the common axis using a spacing depending on the number of blades in the blade stage; and
inspecting the blade stage using the three-dimensional virtual rendering.

11. The system of claim 10, wherein the inspecting includes:
identifying at least one of an axial deformation, a radial deformation, a twist deformation, and a contact gap violation, and
further comprising modifying at least one blade to at least reduce the at least one of the axial deformation, the radial deformation, the twist deformation, and the contact gap violation.

12. The system of claim 10, wherein the extracting the geometric location data includes:
identifying x coordinates of a pair of corresponding axial reference points of the hard face planes for each pair of adjacent shrouds in space; and
wherein the inspecting includes:
measuring an axial overlap between hard face planes of each pair of adjacent blades in the three-dimensional virtual rendering based on the x coordinates of the pair of corresponding axial reference points, and
identifying an axial deformation by determining whether an axial overlap individually exceeds a threshold.

13. The system of claim 12, wherein the measuring the axial overlap includes calculating an axial areal overlap, and the determining includes determining whether one or more axial areal overlaps exceed a threshold.

14. The system of claim 10, wherein the extracting the geometric location data includes:
identifying, for each shroud in space, a z coordinate of a selected radial point chosen from the group consisting of an outermost radial point of a hard face plane and an innermost radial point of the hard face plane; and
wherein the inspecting includes:
measuring a radial shift between the selected radial point of each pair of adjacent blades in the three-dimensional virtual rendering, and
identifying a radial deformation by determining whether one or more radial shifts individually exceed a threshold.

15. The system of claim 14, wherein the measuring the radial shift includes calculating a radial areal overlap, and the determining includes determining whether a radial areal overlap individually exceeds a threshold.

16. The system of claim 10, wherein the extracting the geometric location data includes:
identifying a pair of x coordinates for each shroud in space; and
wherein the inspecting includes:
measuring a twist amount of each shroud in space by measuring a shift in space of each of the pair of x coordinates thereof relative to an expected location of each x coordinate, and
identifying a twist deformation by determining whether one or more twist amounts individually exceed a threshold.

17. The system of claim 10, wherein the extracting the geometric location data includes:
identifying an x, y and z coordinate of a plurality of vertical reference points along a hard face plane of each shroud in space, and
identifying an angular orientation of each hard face plane in space; and
wherein the inspecting includes:
measuring a contact gap between hard face planes of each pair of adjacent blades in the three-dimensional virtual rendering at each of the plurality of vertical reference points on each hard face plane,
identifying a minimum contact gap amongst the contact gaps at each of the plurality of vertical reference points, and
identifying a contact gap violation by determining whether the minimum contact gap exceeds a threshold.

18. The system of claim 10, further comprising:
based on the inspecting, changing a circumferential position of at least one blade within the blade stage within the three-dimensional virtual rendering of the shrouds of the blade stage; and
ensuring a moment weight balancing of the blade stage does not exceed a threshold.

19. A system for virtually inspecting a blade stage, the blade stage having known dimensions, the system comprising:
a digitizing device for obtaining a three-dimensional model of at least a shroud of each blade of the blade stage;
a computer system including at least one module configured to perform the following processes:
extracting a geometric location data of a plurality of reference points of each shroud from a three-dimensional model of a shroud of each blade of the blade stage created by digitizing using a digitizing device;
generating a three-dimensional virtual rendering of the shrouds of the blade stage based on the geometric location data and the known dimensions of the blade stage, the three-dimensional virtual rendering including a rendering of the plurality of reference points of each shroud, wherein the generating includes:
radially positioning each shroud relative to a common axis based on a shroud radius of the blade stage, and circumferentially positioning each shroud about the common axis using a spacing depending on the number of blades in the blade stage, inspecting the blade stage using the three-dimensional virtual rendering by identifying at least one of an axial deformation, a radial deformation, a twist deformation, and a contact gap violation; and modifying at least one blade to at least reduce the at least one of the axial deformation, the radial deformation, the twist deformation, and the contact gap violation.

20. The system of claim 19, wherein the extracting the geometric location data includes:

identifying x coordinates of a pair of corresponding axial reference points of the hard face planes for each pair of adjacent shrouds in space; and wherein the inspecting includes:

measuring an axial overlap between hard face planes of each pair of adjacent blades in the three-dimensional virtual rendering based on the x coordinates of the pair of corresponding axial reference points, and identifying the axial deformation by determining whether one or more axial overlaps individually exceed a threshold.

* * * * *